United States Patent [19]

Wolff et al.

[11] Patent Number: 4,830,003
[45] Date of Patent: May 16, 1989

[54] COMPRESSIVE STENT AND DELIVERY SYSTEM

[76] Inventors: Rodney G. Wolff, 468 W. Eagle Lake Dr., Maple Grove, Minn. 55369; Creg W. Dance, 812 Benton St., Anoka, Minn. 55303; Brice Letac, 134 rue du Renard, 76.000 Roven, France; Alain Cribier, 76150 Maromme, Maromme, France

[21] Appl. No.: 208,252

[22] Filed: Jun. 17, 1988

[51] Int. Cl.$^4$ ............................................. A61M 29/00
[52] U.S. Cl. ........................................ 128/343; 623/1
[58] Field of Search ............ 623/1; 600/37; 128/343, 128/334 R, 335

[56] References Cited

U.S. PATENT DOCUMENTS

| | | | |
|---|---|---|---|
| 4,503,569 | 3/1985 | Dotter | 128/303 |
| 4,553,545 | 11/1985 | Maass et al. | 128/341 |
| 4,580,568 | 4/1986 | Gianturco | 128/348 |
| 4,647,416 | 3/1987 | Seiler | 623/1 |
| 4,649,922 | 3/1987 | Wiktor | 128/344 |
| 4,655,771 | 4/1987 | Wallsten | 128/343 |
| 4,733,665 | 3/1988 | Palmaz | 128/343 |

OTHER PUBLICATIONS

Palmaz et al., Expandable Intraluminal Vascular Graft: A Feasibility Study, Feb., 1986, Surgery, pp. 199-205.
Palmaz et al., Expandable Intraluminal Graft: A Preliminary Study, 1985, Radiology, pp. 73-77.
Palmaz et al., Atherosclerotic Rabbit Aortas: Expandable Intraluminal Grafting, 1986, Radiology, pp. 723-726.

Primary Examiner—Richard J. Apley
Assistant Examiner—James Prizant

[57] ABSTRACT

A cylindrical shaped stent to prevent arterial acute closure and subsequent restenosis formed of longitudinal wires of biocompatible metal. The wires are welded together in pairs at alternate ends with each pair of wires bent into a V-section. The wires are all formed into a cylinder welded closed to form the stent. The stent is compressed and loaded into an outer catheter by a special tool. The stent is positioned and released for self expansion in situ by an inner catheter. A guide wire through both assists in threading the catheters through blood vessels.

10 Claims, 2 Drawing Sheets

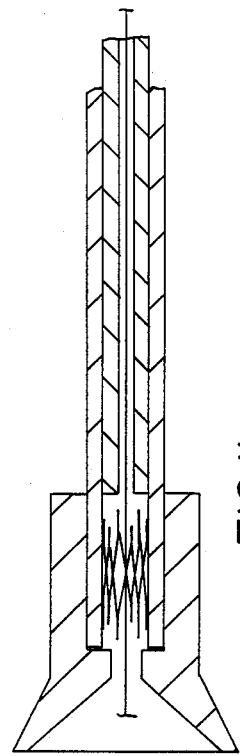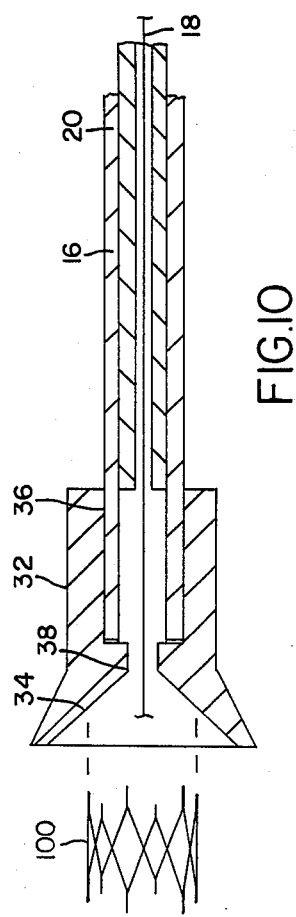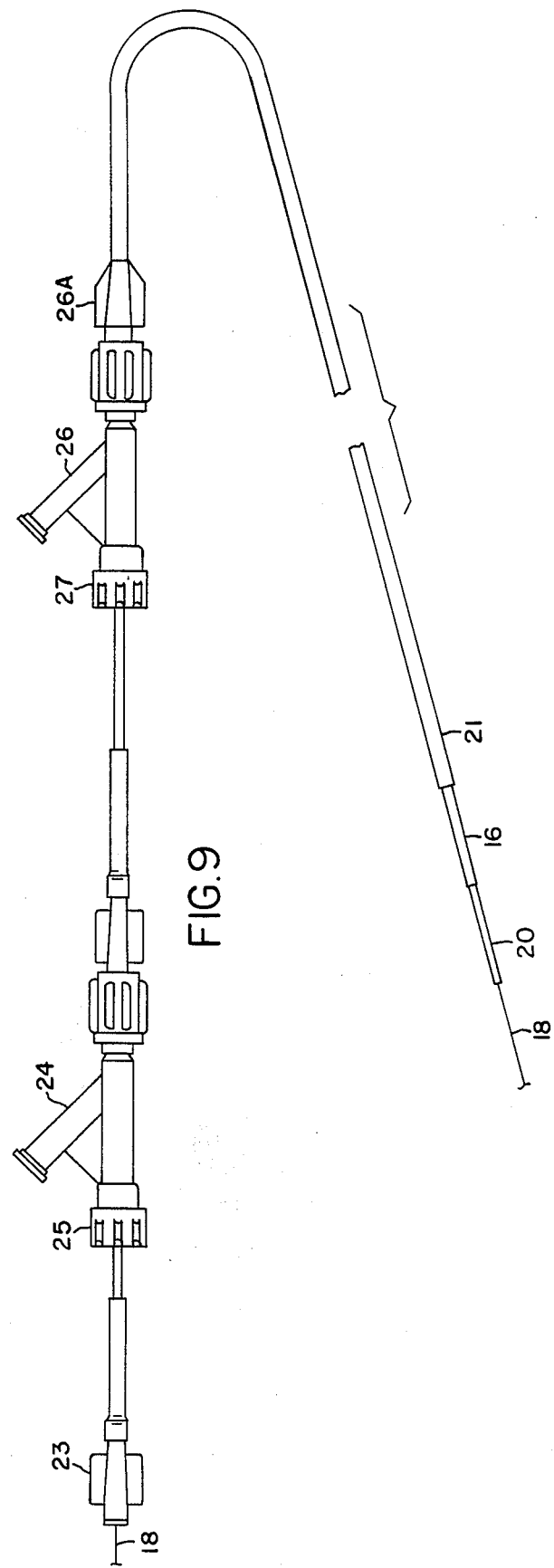

COMPRESSIVE STENT AND DELIVERY SYSTEM

TECHNICAL FIELD

The present invention relates to an intravascular stent which can be applied within the peripheral or coronary arteries of a living animal or human being to maintain patency after a balloon angioplasty, either a percutaneous transluminal coronary angioplasty (PCTA) or a percutaneous transluminal angioplasty (PTA) procedure. The stent comprises a tubular shaped structure made up of individual wires welded together which can be compressed along the axis to a smaller tubular diameter to fit within an outer catheter to hold the stent compressed, which is used along with an inner catheter to release the stent and a guide wire which are used after a balloon angioplasty to insert, position and fix the stent permanently at the angioplasty site to prevent acute reocclusion and subsequent restenosis. The construction of the stent is such that the dimensions and material of the device can be selected to provide a given radial force against the interior of the artery adequate to maintain the shape of the vessel against any force tending to close it. These closure forces include not only acute reclosure due to intimal dissections, flaps and spasm but also plaque restenosis. The latter is prevented or slowed by neo-intimal overgrowth on the stent itself. The length of the stent can also be varied or more than one stent can be used at a single location to accommodate curvature and other unusual arterial characteristics. Radiopaque marker material on the end of the inner and outer catheters permits locating the stent at the desired site by external monitoring or the stent itself can be made of radiopaque material.

BACKGROUND ART

In U.S. Pat. No. 4,553,545 a device which can be expanded after insertion in a blood vessel by rotating a wire coil about its length to reduce the number of turns and thereby increase the diameter is disclosed. In U.S. Pat. No. 4,503,569 a helically wound coil is formed of a memory Nitinol alloy which has a transition temperature in the range of 115 degrees to 125 degrees Farenheit. After placement in the vessel this coil is heated to regain its original larger shape. These approaches require either heat or mechanical forces to be applied to the apparatus, in order to expand the stent at the site, with the resulting trauma to the body.

In U.S. Pat. No. 4,580,568 a stent is formed of stainless steel wire of 0.018 inches diameter arranged in a closed zig-zag pattern. The stent is compressed to reduce its size in order to position it within a sheath, which is used to locate the stent within the vascular system. A flat-ended catheter is used through the sheath to hold the stent in place in the passageway while the sheath is withdrawn, allowing the stent to expand into its original shape to hold the passageway open and enlarged. According to the specifications the only energy stored in this stent to restore it to its original shape is stored in the bends.

This device and delivery system suffers from a number of severe limitations and problems. Fashioning the stent from a continuous wire folded in a zig-zag fashion requires a sharp bend in the wire at each end of the stent to form this shape. A wire can only be bent at a ratio which is some multiple of the wire diameter. The exact multiple will vary according to the property of the material. The example cited in the patent as claimed uses a wire of 0.018 inches in diameter which is equivalent to 0.04572 centimeters and a bend ratio of no more than 0.2 centimeters. This is a ratio of approximately 1 to 4.37. Since the wire is bent to form the zig-zag shape there must be some angle formed between adjacent legs which limits the minimum spacing between these legs. A large amount of force is necessary to compress the stent when the stent is short since energy is only stored in the bends. If the stent is made relatively short in length with respect to the diameter then the amount of force necessary to bend the wires in order to compress the stent becomes large. This again is because the bends are the only place that energy is stored. Only if the stent is made relatively long with respect to the diameter is the force required to hold a vascular vessel open reduced. The claims specified stents of specific sizes 5.5 cm long×4 cm diameter fully expanded and 3.0 cm long×2.5 cm diameter fully expanded. This relatively long length and diameter results in forces which are compatible with the vascular system but can obviously only be used in very large peripheral arteries and veins. Another effect is the absolute minimum size to which the stent can be compressed. As mentioned earlier the angular relationship between adjacent wires at the ends limits the minimum spacing between adjacent wires which in turn limits the minimum diameter of the stent to a size which is incompatible with coronary arteries and like sized vessels.

In addition, since the diameter of the wire and the material composition is continuous throughout its length, these parameters are not varied to provide different characteristics at the bends vs. the straight section of the zig-zag. Since only the material in the bends themselves are involved in storing energy the characteristics of the bends versus the straight sections are not necessarily compatible for all of these requirements in particular when the additional necessity for utilizing a bio-compatible material is added. Further, to complete and close the zig-zag pattern made up of a single wire a sleeve must be placed over the two ends to connect them together which results in an anomoly at that point.

We have taken an entirely different approach to the problem to avoid these inherent limitations of the previous system by using individual parts welded together to avoid the necessity for a bend in the material completely. This overcomes all of the limitations and restrictions enumerated above. Our stent is adaptable for use in coronary arteries with their extremely small diameter where the other approach because of the bend diameters results in a stent which cannot be reduced to the required coronary size, unless a far fewer number of wires are used. If far fewer numbers of wires are used, this greatly limits both the force applied to and the surface coverage of the vessel wall.

The delivery system has no means of locating the position of the stent relative to the stenosis site from the exterior of the body. No guide wire is used and in use the stent is inserted from the proximal end of the catheter.

SUMMARY OF THE INVENTION

The present invention is characterized by a prothesis stent which is useful in conjunction with a balloon angioplasty, either a percutaneous transluminal coronary angioplasty (PCTA) or a percutaneous transluminal angioplasty (PTA) of diseased coronary arteries or any other larger arteries to prevent acute reclosure or restenosis of the artery after the procedure. The stent is applied immediately after the balloon angioplasty as an extension of the procedure. The stent is in the form of an open ended tube formed by a set of angled wires which are welded together at the ends resulting in an offset angle, then formed into a tubular shape and the end wires welded together. Using this construction the wires are connected obliquely from one end to the opposite end. The wires are made of spring material which can be bent closer together to form a smaller diameter tube and will store energy in the straight segments, but when the compressive force is removed the wires will be urged by the force from the oblique wires to self expand to the original tubular diameter. This restoring force must be adequate to maintain the artery in an expanded position as well as resist all other forces tending to close the artery. The stent structure chosen results in a small percentage of this structure supporting the artery to allow tissue overgrowth of a neointimal lining to prevent or retard restenosis from the plaque or other fibrotic growths. The stent is inserted percutaneously using an outer catheter to enclose and compress the stent, and an inner catheter which has the same size and the same diameter as the compressed stent to release the stent. A guide wire through the inner catheter assists in positioning the stent at the stenosis site while an optional guide catheter over the outer catheter aids in inserting the inner and outer catheters into the artery. The guide wire can be the same guide wire used in the previous balloon angioplasty. The location of the stent itself is determined by monitoring radiopaque markers on the catheter ends using a fluroscope or similar device to permit locating the stent at the proper site. The stent itself can also be made of radiopaque material, such as platinum or platinum iridium to readily permit locating the stent at the stenosis site using the same fluroscope techniques. The stent ensures patency and prevents acute reocclusion and restenosis at this location.

BRIEF DESCRIPTION OF THE DRAWINGS

FIG. 9 shows the inner and outer catheters and guide wire assembled together with the Y-connector hemostasis valves and guiding catheter.

FIG. 10 is a cross-section view of the stent loading tool in position for loading the stent into the outer catheter.

FIG. 11 is the cross-section view of FIG. 10 with the stent loaded into the outer catheter.

DESCRIPTION OF THE PREFERRED EMBODIMENT

Figure 1:
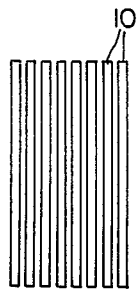
FIG. 1 is a front view of the individual wires aligned for attachment.
Figure 2:
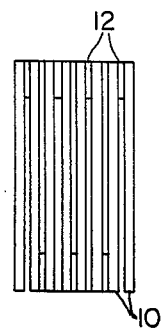
FIG. 2 is a front view of individual wires welded together.

Referring to FIG. 1, individual wires 10 making up the device are shown before bending and shaping. In FIG. 2 welds 12 are shown connecting alternate ends of wires 10. The wires used can be any of the biocompatible metals. Biocompatible metals include some 300 series stainless steels, such as 316LSS, platinum and platinum-irridium alloys, certain cobalt-chromium alloys such as MP35N, and unalloyed titanium. The welds typically range in length from 1 to 2 millimeters for coronary artery applications. As an example, a Nd/YAG laser can be used at approximately 5 watts power to accomplish this weld although it is also possible to use other weld processes here such as resistance welding.

Figure 3:
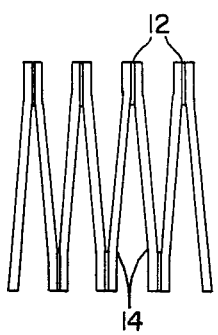
FIG. 3 is a front view of the welded wire bent prior to being formed into a cylinder.
Figure 4:
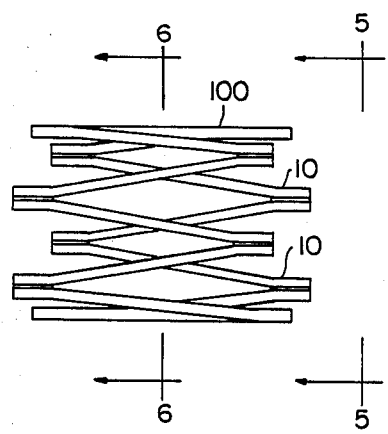
FIG. 4 is a side view of the stent.

In FIG. 3 bends 14 in wires 10 form a "V" at each weld 12. Twelve of these wires 10 shaped and welded together as shown in FIG. 3 are shown in FIG. 4 formed into a cylindrical configuration to form a tubular shaped stent 100 with cylinder completed by welding together the end wires. Bends 14 can be set after wires 10 are welded as illustrated in FIG. 3 or can be set before the weld, in either case the wires are spaced apart by these bends such that only a small percentage of the cylinder surface area, on the order of 10 to 25 percent, is made up of metal. The advantages of this minimal metal surface area will be discussed later.

This method of forming stent 100 permits utilizing any desired wire with any required characteristics since the ends of the wires are simply welded together. As an alternative, wires 10 can be bent to the desired angle, the bent wires formed and held into a cylinder shape, and the total structure welded closed using simple jigs and fixtures. The variables permitted by this approach include wire size, material used, wire length, weld length, the angle of bend and the cylinder diameter. For coronary arteries wires as small a 0.004 inches in diameter can be used with wire lengths which range from 4 to 15 millimeters and stent diameters of from 2 to 5 millimeters. The number of wires used in such coronary stents can vary from 8 to 16 over the range of stent diameters. These extremely small sizes which are necessary for coronary artery applications, can be readily manufactured and tailored for any desired coronary artery requirement. These ranges of wire size and stent size permit the external metal surface area of typically 10 to 25 percent of the total cylinder area stated above.

The larger peripheral arteries can utilize a wire diameter of 0.006 to 0.016 inches with a length of 10 to 25 millimeters and a stent diameter of 5 to 15 millimeters. The number of wires used here will vary from 8 to 16 over the range of stent diameters.

Figure 5:
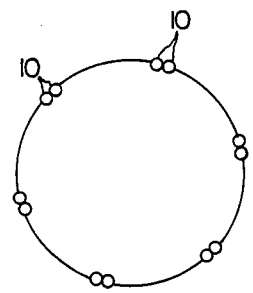
FIG. 5 is a schematic representation of FIG. 4 taken along 5—5.

In FIG. 4 a side view of stent 100 is shown. This illustrates the tubular shape which the individual wires 10 form. FIG. 5 shows the uniform spacing between pairs of wires 10 at the ends where the wires are welded together while FIG. 6 shows the uniform spacing between the individual wires at the center of the stent length.

Figure 7:
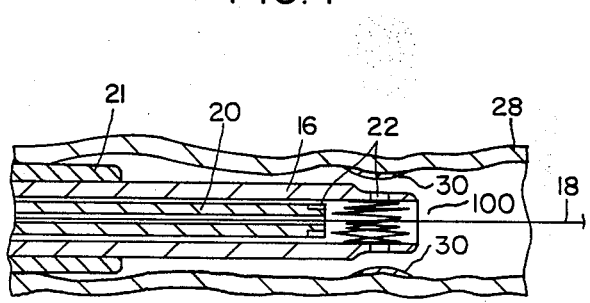
FIG. 7 is a longitudinal-section of an artery with inner catheter, outer catheter, guide wire and loaded stent before placing stent in artery.
Figure 6:
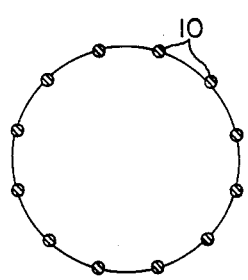
FIG. 6 is a schematic representation of FIG. 4 taken along 6—6.

In FIGS. 4, 5, and 6 stent 100 is shown completely unrestrained with wires 10 at their maximum separation storing no energy. In FIG. 7, stent 100 is shown compressed and enclosed within an outer catheter 16 with a guide wire 18 threaded through the longitudinal axis of stent 100. Stent 100 is sized such that the wire 18 will readily pass through the stent when it is compressed.

Figure 8:
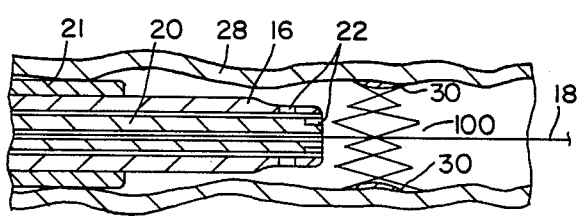
FIG. 8 is the view of FIG. 7 after placing stent in artery by retracting outer catheter and releasing the stent.

An inner catheter 20 is sized to fit within outer catheter 16 but is sized and of materials such that inner catheter will readily slide within the outer catheter. Radiopaque markers 22 at the ends of both inner catheter 20 and outer catheter 16 provides a capability of determining the location of these catheters by using X-ray excitation and a fluoroscope monitoring device external to the body. An optional guide catheter 21 encloses outer catheter 16. All of these items are inserted within an artery 28, as will be described later. Artery 28 has a stenosis site 30 which encircles the artery. In FIG. 8 stent 100 is shown released from outer catheter 16 supporting stenosis site 30. The equipment and procedure used to accomplish the release of stent 100 at stenosis site 30 will be described later.

In FIG. 9 the assembly of inner catheter 20, outer catheter 16, guide wire 18 and guide catheter 21 are shown. Standard Y-connector hemostasis valves 24 and 26 in conjunction with respective valve adjuster caps 25 and 27 control bleeding. Hemostasis valve 24 has a centered hole sized to permit inner catheter 20 to slide through. Hemostasis valve 26 has a centered hole to permit outer catheter 16 to slide through. Hub 23 has a centered hole sized to permit guide wire 18 to slide through. This arrangement permits inner catheter 20 and outer catheter 16 to slide relative to each other, whenever caps 25 and 27 are loosened which frees respective O-rings in each, not shown, from a closed position to permit the adjacent parts to slide. After the adjustments are made caps 25 and 27 are again tightened which again closes the O-rings against the adjacent parts which again prevents relative movement and seals against blood loss. Guide catheter 21 encloses outer catheter 16 and is secured to hemostasis valve 26 by proximal hub 26A.

In use a balloon angioplasty procedure is performed on the artery 28 shown in FIG. 7 to expand, remodel, or enlarge the vessel lumen through stenosis site 30. Guide wire 18 and guide catheter 21 can be the same items used in the balloon angioplasty and left in place to guide outer catheter 16. After the balloon angioplasty procedure then guide wire 18, inner catheter 20, outer catheter 16 and stent 100 are assembled as shown in FIGS. 7 and 9 and located within artery 28 with the stent previous loaded in the end of the outer catheter, and the inner catheter bearing just proximal to the stent with the outer catheter enclosed in guide catheter 21, as shown in FIG. 9. The method of loading stent 100 in this fashion will be described later. All of these parts are previously sterilized then threaded through the vessels in the same manner and using the same path as that used for the balloon angioplasty procedure while monitoring the location of radiopaque markers 22 by illuminating the site by x-ray and observing the markers by a fluoroscope adjacent to the site. The stent 100, if made from one of the radiopaque materials, can also be monitored to determine its location.

Guide wire 18 is run inside inner catheter 20 and both the inner and outer catheter 20 are locked together at their proximal ends during the insertion and location of stent 100 at the stenosis site by tightening valve caps 25 and 27 as discussed earlier and illustrated in FIG. 9. Since inner catheter 20 bears against the proximal end of stent 100 as shown in FIG. 7, this will insure that the stent is held in the same relative position with respect to locked catheters 16 and 20 during this insertion and location of stent 100 within stenosis site 30. The distance from the end of inner catheter 20 and outer catheter 16 to stent 100 is known, consequently the location of the distal end of the stent can be determined. Further, as discussed earlier, if stent 100 itself is made radiopaque, it can readily be located by a fluoroscope. Guide wire 18 being more flexible than catheters 16 and 20 is used to steer the catheters into the artery. Guide catheter 21 is previously positioned just adjacent to the artery, and the remainder of the assembly slid through the guide catheter to complete the procedure. A fluoroscope adjacent the patient's body indicates when stent 100 is located adjacent stenosis site 30 in the position shown in FIG. 7. Then valve cap 25 is loosened, inner catheter 20 held in position by hub 23 and valve 24 moved proximally to withdraw outer catheter 16 from about the inner catheter until the stent is released as shown in FIG. 8. During this process inner catheter 20 holds stent 100 in place as outer catheter 16 is withdrawn. When stent 100 is released from outer catheter 16 the stent will self expand as shown to support and fixate against the area of stenosis site 30. After stent 100 is released then the entire assembly is withdrawn leaving only the stent in place within the vessel. This simple procedure requires only the same general catheterization techniques as the balloon angioplasty to locate stent 100 at the stenosis site.

Placement of stent 100 is thus a complimentary procedure to a balloon angioplasty which is performed during the same catheterization and which lengthens the balloon angioplasty procedure by only a few minutes. This brief extension of time results in this procedure being well tolerated by the body. When stent 100 expands it bears against the interior wall of the vessel at stenosis site 30 to provide a radial outwardly directed force in all directions.

This force has two major effects. One effect is to hold the vessel open against any inner directed force, such as spasm, and essentially tacks up intimal flaps or dissections generated by prior balloon angioplasty to assure the patency of the vessel. This force is tailored by a selection of the parameters which were discussed earlier. The second effect of this force is to securely fixate wires 10 within the interior wall of vessel 28. This second effect will assist in the early regeneration of tissue overgrowth or neointimal over the wires 10 of stent 100 making restenosis less likely. The small percentage of metal surface area, noted earlier, permits this early regeneration, and also aids in prevention of acute closure due to thrombosis.

As mentioned earlier, the spring force developed by wires 10 is tailored for the given procedure. The force must be sufficient to maintain artery 28 fully open and to also resist vasoconstrictive forces, spasm and the possible progressive development of an additional plaque buildup at the location of stenosis site 30. The force must not be excessive beyond these requirements however to avoid traumatization of the vessel wall.

The diameter of stent 100, when squeezed to fit within outer catheter 16, is reduced from two to six times in size. This range of size adjustments plus the variation in spring constant possible permits the adjustment of the expansion forces to the amount desired.

As mentioned, typical sizes for stent 100 have a range from a minimum external diameter of 2 to 4 millimeters when compressed to fit within outer catheter 16 to 5 to 15 millimeters when released within a large arterial vessel, to a range from a minimum external diameter of 1 to 1½ millimeters when compressed within outer catheter 16 to 2 to 5 millimeters when released within the coronary arteries.

The length of stent 100 is likewise adapted to the length of the stenosis, which may be quite variable from one case to the other, but should always be longer than the stenotic segment. To make the applications of stent 100 more flexible, in case of tortuosities or angulations of the vessel at or before the plaque or lesions site, the stent can be made shorter than the stenosis with two or more stents placed in series to each other at the curved vessel site or in outer catheter 10 so that an angulation of the catheter can be obtained at the point between the end-to-end stents.

In order to load stent 100 into outer catheter 16 a special generally cylindrically shaped tool 32 is utilized. Tool 32, shown in cross section in FIG. 10, has a flared opening 34 extending inwardly from one end of the cylinder and a circular bore 36 from the outer end with a flat 38 between the two. Outer catheter 16 is inserted within tool 32 to the bottom of bore 36, and inner catheter 20 is positioned just short of entering the bore while guide wire 18 extends completely through the tool through both the bore and flared opening 34 of tool 32. Outer catheter 16, inner catheter 20 and guide wire 18 are locked together in this relationship using valve caps 25 and 27 in the manner previously described. Stent 100 is then pushed through flared opening 34 which guides the stent past flat 38 into bore 36 where it will spring open in the bore, as shown in FIG. 11, to complete the loading operation. Tool 32 is then removed from about outer catheter 16.

The stent is easy to fabricate and because the wires are attached together by welding the wire size and material can be selected based only upon the desired radial force and vessel size. Since welding results in a zero spacing between the wires at the point of attachment any size wire can be welded. The extremely small stents necessary for the coronary arteries can thus be readily fabricated using this technique.

The use of a radiopaque material as a marker on the ends of the outer and inner catheters permits locating the stent precisely using only a fluoroscope, as does using a radiopaque material for the stent itself. The use of an inner catheter which has a circular cross-section to positively engage the stent inside the outer catheter assures that the stent will be released easily because the expansion forces of the compressed stent will cause it to bear against the inner wall of the outer catheter. This device is simple in construction with parameters which can readily be adapted to meet any requirement.

The use of Y connector hemostasis valves 24 and 26 permits the injection of liquid containing radiopaque dye if it is necessary to determine the shape and size of the artery at the location of stent 100. If desired guide wire 88 can be removed after stent 100 is in place and this space used to inject liquids.

While this invention has been described with reference to an illustrative embodiment, this description is not intended to be construed in a limiting sense. Various modifications of the illustrative embodiment, as well as other embodiments of the invention, will be apparent to persons skilled in the art upon reference to this description. It is therefore contemplated that the appended claims will cover any such modifications or embodiments as fall within the true scope of the invention.

What is claimed is:

1. A stent comprising:
   (a) a number of equally dimensioned and shaped wires each having an essentially straight center segment with end segments bent at oblique angles with respect to said center segment such that opposite said end segments of each said wire are essentially parallel one end segment to the other; and
   (b) said wires oriented and equally spaced to form a tubular shape said bent end segments of each wire oriented parallel, over lapping and contiguous with each adjacent wire, resulting in an acute angle being formed by said center segments of each adjacent pair of wires, being secured together at all end segments; and
   (c) said wires fashioned from spring metal biocompatible material, such that said wires can be bent to store energy in said wire segments to permit reducing the diameter of said stent to permit inserting said stent into an outer catheter sized to receive said stent when compressed to permit placing said stent percutaneously within a living organism.

2. The structure as in claim 1 and further comprising an inner catheter sized to slideably fit within an outer catheter with the walls of said inner catheter sized to bear against the end of said stent when said inner catheter is fit within said outer catheter and said stent compressed to fit within said outer catheter.

3. The assembly as in claim 2 wherein said inner and outer catheter are tipped with a radiopaque marker at their distal ends adjacent to said stent.

4. The structure as in claim 2 wherein a guide wire is threaded coaxially through said inner catheter and said stent and wherein said inner catheter and said stent are sized to permit said guide wire to be slid through their respective centers as an aid in threading said catheters through a circulatory system.

5. The structure as in claim 4 wherein said outer catheter is threaded coaxially through a guide catheter sized to slideably receive said outer catheter to provide guiding means in said circulatory system for said outer and inner catheter.

6. The structure as in claim 4 wherein said inner catheter can be slideably locked and sealed to said outer catheter by means of a first Y-connector hemostasis valve and said guide wire is exposed at the proximal end to permit slideable adjustment of said guide wire with respect to said inner catheter.

7. The structure as in claim 5 wherein said inner catheter can be slideably locked and sealed to said outer catheter by means of a first Y-connector hemostasis valve and said outer catheter can be slideably locked and sealed to said guide catheter by means of a second Y-connector hemostasis valve and said guide wire is exposed at the proximal end to permit slideable adjustment of said guide wire with respect to said inner catheter.

8. The assembly as in claim 1 wherein said wires are secured together by welding.

9. The combination of claim 2 further comprising a generally cylindrical shaped tool having an axial bore from a first end and a flared axial opening from a second end joined by a coaxial segment, said tool being sized to provide a means for loading said stent within said outer catheter.

10. The assembly as in claim 1 wherein said wires are made of a radiopaque material.

* * * * *